(12) United States Patent
Tsao

(10) Patent No.: US 7,462,487 B2
(45) Date of Patent: Dec. 9, 2008

(54) CELL CULTURE MEDIA

(75) Inventor: Mary C. Tsao, Burlingame, CA (US)

(73) Assignee: Raven biotechnologies, inc., South San Francisco, CA (US)

( * ) Notice: Subject to any disclaimer, the term of this patent is extended or adjusted under 35 U.S.C. 154(b) by 200 days.

(21) Appl. No.: 10/944,083

(22) Filed: Sep. 17, 2004

(65) Prior Publication Data

US 2005/0101011 A1    May 12, 2005

Related U.S. Application Data

(60) Provisional application No. 60/504,674, filed on Sep. 18, 2003.

(51) Int. Cl.
*C12N 5/00* (2006.01)
*C12N 5/06* (2006.01)
*C12N 5/08* (2006.01)

(52) U.S. Cl. .................... 435/404; 435/420; 435/253.6; 435/256.8

(58) Field of Classification Search .................. 435/404
See application file for complete search history.

(56) References Cited

U.S. PATENT DOCUMENTS

| | | | | |
|---|---|---|---|---|
| 3,308,038 | A | * | 3/1967 | Rhodes et al. .............. 435/242 |
| 5,316,938 | A | * | 5/1994 | Keen et al. .................. 435/404 |
| 5,756,291 | A | | 5/1998 | Griffin et al. |
| 5,814,482 | A | | 9/1998 | Dubensky, Jr. et al. |
| 5,834,312 | A | | 11/1998 | Wille, Jr. |

FOREIGN PATENT DOCUMENTS

WO    WO-2005/028626 A2    3/2005

OTHER PUBLICATIONS

Freshney R. I. In: "Culture of Animal Cells. A Manual of Basic technique". Alan R. Liss, Inc., New York. 1987, pp. 74-84.*
Barngrover, D. et al. (1985). "High Density Mammalian Cell Growth in Leibovitz Bicarbonate-Free Medium: Effects of Fructose and Galactose on Culture Biochemistry," *J. Cell Sci.* 78:137-189.
Bottenstein, J. et al. (1979). "The Growth of Cells in Serum-Free Hormone-Supplemented Media" Chapter 6 In *Methods in Enzymology* Academic Press, Inc.: New York, NY. 58:94-109.
Bouwens, L. et al. (Nov. 1994). "Cytokeratins as Markers of Ductal Cell Differentiation and Islet Neogenesis in the Neonatal Rat Pancreas," *Diabetes* 43(11):1279-1283.
Boyce, S.T. et al. (Jul. 1983). "Calcium-Regulated Differentiation of Normal Human Epidermal Keratinocytes in Chemically Defined Clonal Culture and Serum-Free Serial Culture," *J. Invest. Dermatol.* 81(1 Supp.):33s-40s.
Delhotal, B. et al. (Sep. 1984). "Comparative Use of Fructose and Glucose in Human Liver and Fibroblastic Cell Cultures," In Vitro 20(9):699-706.

Delhotal-Landes, B. et al. (May 1987). "Comparative Metabolic Effects of Fructose and Glucose in Human Fibroblast Cultures," *In Vitro Cell Dev. Biol.* 23(5):355-360.
Evans, V.J. et al. (1964). "Chemically Defined Media For Cultivation of Long-Term Cell Strains From Four Mammalian Species" In *Experimental Cell Research* Academic Press, Inc. 36:439-474.
Franke, W.W. et al. (1982). "Formation of Cytoskeletal Elements During Mouse Embryogenesis. III. Primary Mesenchymal Cells and the First Appearance of Vimentin Filaments," *Differentiation* 23(1):43-49.
Gibson, U.E.M. et al. (1996). "A Novel Method for Real Time Quantitative RT-PCR," *Genome Research* 6:995-1001.
Kahn, H.J. et al. (Feb. 15, 1983). "Categorization of Pediatric Neoplasms by Immunostaining with Antiprekeratin and Antivimentin Antisera," *Cancer* 51(4):645-653.
Loo, D.T. et al. (Apr. 10, 1987). "Extended Culture of Mouse Embryo Cells Without Senescence: Inhibition by Serum," *Science* 236:200-202.
Low, K. et al. (1985). "Growth Kinetics of Hybridoma Cells: (2) The Effects of Varying Energy Source Concentrations," *Dev. Biol. Stand.* 60:73-79.
Mather, J.P. et al. (1979). "The Growth of Mouse Melanoma Cells in Hormone-Supplemented, Serum-Free Medium" In *Experimental Cell Research* Academic Press, Inc. 120:191-200.
Mochizuki, K. et al. (1993). "Enhanced Production of Human Monoclonal Antibodies by the Use of Fructose in Serum-Free Hybridoma Culture Media," *Cytotechnology* 13(3):161-173.
Mochizuki, K. et al. (1993). "Enhanced Production of Human Monoclonal Antibodies by the Use of Fructose in Serum-Free Hybridoma Culture Media," *Cytotechnology* 13(3):161-173.
Tsao, M.C. et al. (Jan. 1982). "Clonal Growth of Normal Human Epidermal Keratinocytes in a Defined Medium," *J. Cellular Physiology* 110(1):219-229.
Wille, J.J. Jr. et al. (Oct. 1984). "Integrated Control of Growth and Differentiation of Normal Human Prokeratinocytes Cultured in Serum-Free Medium: Clonal Analyses, Growth Kinetics, and Cell Cycle Studies," *J. Cellular Physiology* 121(1):31-44.
Wolfrom, C. et al. (Dec. 1983). "Comparative Effects of Glucose and Fructose on Growth and Morphological Aspects of Cultured Skin Fibroblasts" In *Experimental Cell Research* Academic Press, Inc. 149(2):535-546.

(Continued)

*Primary Examiner*—Vera Afremova
(74) *Attorney, Agent, or Firm*—Morrison & Foerster LLP

(57)    ABSTRACT

Methods are taught for culturing mammalian cells, preferably human cells, to improve production of proteins, recombinant or endogenous. Methods are also provided for the growth and long-term survival of cell lines, particularly cell lines established from primary culture. Cell culture media are also provided, contained varying levels of selected amino acids, supplemented with various growth factors and trace elements. In additionally, the media are optionally serum-free, and preferably use an energy source other than glucose. The media are particularly suitable for the primary culture and long-term culture of human fetal cells.

1 Claim, 3 Drawing Sheets

OTHER PUBLICATIONS

Figure 1:
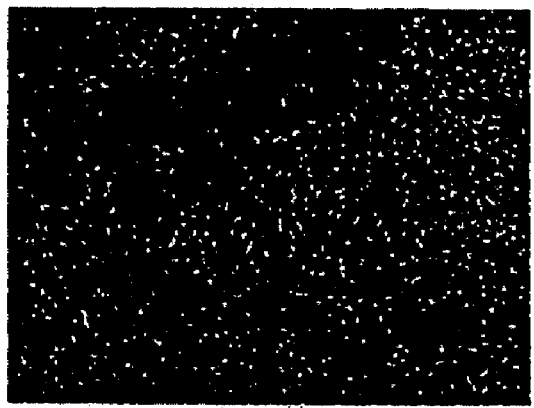
Figure 1:
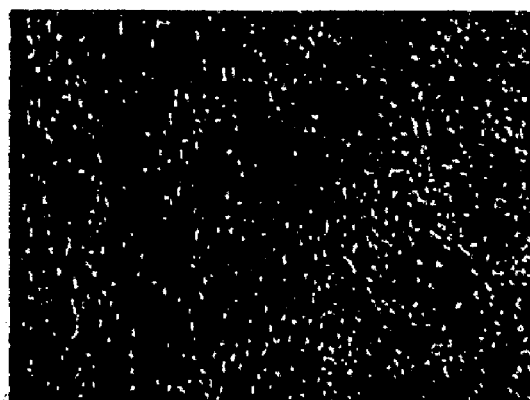
Figure 1:
Figure 1:
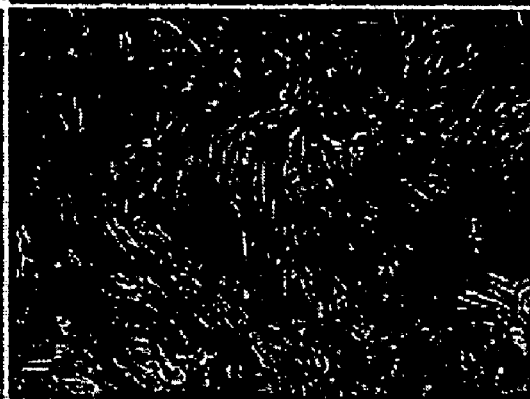

International Search Report for PCT/US04/30404 filed Sep. 17, 2004, mailed Jun. 7, 2005, 4 pages.

Kwun, J. et al. (Jun. 2003). "Effects of Exogenous Hexoses on Bovine In Vitro Fertilized and Cloned Embryo Development: Improved Blastocyst Formation After Glucose Replacement with Fructose in a Serum-Free Culture Medium," *Molecular Reproduction and Development* 65(2):167-174.

Lemonnier, F. et al. (1987). "Comparative Use of Glucose and Fructose in Cultured Fibroblasts from Patients with Hereditary Fructose Intolerance," *Journal of Inherited Metabolic Disease* 10(1):52-61.

Supplementary European Search Report mailed on Nov. 27, 2007 for EP Application 04 78 4301, filed on Sep. 17, 2004, 4 pages.

Zhaolie C. et al. (Jun. 1996). "A Novel Serum-Free Medium for the Cultivation of Vero Cells on Microcarriers," *Biotechnology Techniques* 10(6):449-452.

\* cited by examiner

Primary Culture

Passage 4

Passage 6

Passage 7

CELL CULTURE MEDIA

CROSS-REFERENCE TO RELATED APPLICATIONS

This application claims the benefit of U.S. provisional application Ser. No. 60/504,674, filed Sep. 18, 2003, which is incorporated in its entirety by reference.

TECHNICAL FIELD

The field of invention is in the field of cell biology. More specifically, it relates to a cell culture medium for propagating cells isolated from human tissues. In particular, it is directed to a serum-free culture medium preferably containing fructose as the major energy source. The medium supports the establishment and growth of primary human cell cultures and may be used for long-term cell culture.

BACKGROUND OF THE INVENTION

The use of in vitro cell culture systems is critical to the field of cell biology and to the understanding of the mechanisms of action underlying human diseases. A wide variety of mammalian cell types have been isolated from mammalian organs and tissues, either from normal tissues or from disease-state tissues, such as tumors and metastases. Different cell types often have individual nutritional requirements and therefore, many distinct media have been developed specifically to meet the nutritional requirement of the different cell types. Many of these media contain sera as an additive, such as FBS (fetal bovine serum), HS (horse serum) and CS (calf serum). The use of serum can be cost prohibitive when culturing cells on a large-scale. Furthermore, the use of serum can be problematic, even on the small-scale, as it contains a number of uncharacterized ingredients that can vary from lot to lot. Additionally, serum contains growth-inhibitory and differentiating factors, as well as de-stabilizing the genetic material leading to genetic changes and eventually senescence (Loo et al., Science 236 (4798):200-2 (Apr. 10, 1987)) of the cells.

The use of a serum-free, chemically defined medium solves all of these problems. F-12:DME (1:1 v/v) was originally developed for the propagation of cells in a chemically defined, serum-free system (Mather et al, *Experimental Cell Research* 120: 191-200,1979; Bottenstein et al, *Methods in Enzymology* 58: 94-109, 1979). This media can be used with a wide variety of cells in conditions with or without sera. Media NCTC-135 is another media formulated for serum-free cell culture growth (Evans et al, *Experimental Cell Research* 36: 439-448, 1964).

Tsao et al. formulated a nutrient medium—designated MCDB 152—supplemented with specified growth factors and hormones for the growth of human epidermal cells (Tsao, M. C. et al., J Cellular Physiology. 110:219-229 (1982)). Further refinements of this medium lead to the development of a medium known as MCDB 153 (see Boyce, S. T. and Ham, R. G., J. Invest. Dermatol. 81:33-40 (1983)). The use of these media lead to a more accurate characterization of the necessary growth factors, hormones and $Ca^{2+}$ requirements for retention of high cloning efficiency which is necessary to maintain proper genetic programming for continued subculture of pluripotent basal epidermal stem cells. See also Wille, J. J. et al., J Cellular Physiol. 121:31-44 (1984) and U.S. Pat. No. 5,834,312, and the various media discussed therein.

Many media for growing cells in culture are described in the literature or are commercially available. Deriving an optimal medium for specific cell culture needs can lead to improvements in cell growth including increased growth rates, growth to high cell densities, controlling the stage and amount of cell differentiation, increasing protein secretion, increased phenotypic and genetic stability, and elimination of senescence for many cell types.

In optimizing cell culture media for growth, modulating the glucose levels can change the ability of cells to grow in a high cell density condition. Glucose levels are also important to the rate of cell proliferation. As cells metabolize in culture, lactic acid is often produced as a by-product of glycolysis. This leads to a rapid drop in pH, eventually causing cell death. The use of fructose in cell culture media as the major carbon energy source theoretically would lead to the decreased production of lactic acid.

Several researchers have compared the metabolic effects of fructose and glucose on growth and morphological aspects of cells such as human fibroblasts. Others have compared fructose and galactose. For example, Delhotal et al. reported four to five times less lactate production when fructose was used instead of glucose in culturing human skin fibroblast and liver cells (In Vitro 20(9): 699-706, 1984). See, also, Delhotal et al., In Vitro Cell Dev Biol. 23(5): 355-60 (May 1987); Wolfrom et al., Exp Cell Res. 149(2):535-46 (December 1983); Barngrover et al., J Cell Sci 78:173-89 (1985); Low et al., Dev Biol Stand 60:73-9 (1985). See also Mochizuki et al., Cytotechnology 13(3): 161-73 (1993), that compares the use cell culture media containing either fructose or glucose for production of human monoclonal antibodies. Despite these research efforts, glucose is still the major carbon energy source in most commercially available cell culture formulations.

While the majority of cell culture studies use established cell lines, the use of primary cell culture is preferable in some cases. Quite often established cell lines are derived from disease-state tissues such as tumors or cells that have undergone chromosomal changes. In order to study properties of cells in vitro that are recently removed from an in vivo situation, primary culture is often needed. Given the complex interactions between cells in an organ or tissue, deriving a primary culture of one specific cell type isolated from tissues can be problematic. Establishing a primary culture of one specific cell type, however, can be achieved through optimization of the nutrients, attachment factors and growth factors present in the culture medium.

Accordingly, it is an object of this invention to prepare a culture media that supports the growth of primary mammalian cell culture from a variety of tissues. Another object of this invention is to provide a culture media that is serum-free and can be used in both small-scale and large-scale cell culture. A cell culture medium that is versatile, yet defined, would be extremely valuable for the purpose of creating new cell lines and resources from a variety of primary tissues.

BRIEF SUMMARY OF THE INVENTION

The invention provides serum-free culture media preferably containing fructose as the major energy source. These culture media are useful for establishing and propagating primary mammalian cells isolated from tissues and for the propagation of established cell lines in culture. The media are particularly suitable for the primary culture and long-term culture of human fetal cells. In certain embodiments, the cells cultured according to the methods of this invention, in the media of this invention, are preferably human fetal pancreatic ductal, kidney tubule, or prostatic epithelial cells.

One method of culturing cells in accordance with the present invention comprises inoculating a cell culture system with cells, and maintaining the cell culture system under conditions suitable to promote cell growth. A population doubling time of from about ten (10) to about forty (40) hours characterizes cell growth achieved in such methods. Furthermore, cells may be cultured serially to achieve a desired number of population doublings.

In preferred embodiment, the media is referred to herein as I3F and contains a selected combination of basic medium nutrients, fructose, and certain divalent salts.

In one particularly preferred embodiment of I3F media, the following components are present at the indicated final concentrations: calcium chloride at 180 mg/L, potassium chloride at 298 mg/L, potassium nitrate at 0.0126 mg/L, magnesium sulfate at 68 mg/L, magnesium chloride at 37 mg/L, sodium chloride at 6200 mg/L, sodium bicarbonate at 1200 mg/L, sodium phosphate at 43 mg/L, sodium phosphate (dibasic) at 88 mg/L, sodium selenite at 0.0126 mg/L, ammonium metavanadate $3.51 \times 10^{-4}$ mg/L, molybdic acid at $3.72 \times 10^{-3}$ mg/L, cupric sulfate at $7.5 \times 10^{-4}$ mg/L, ferrous sulfate at 0.25 mg/L, manganese sulfate at $4.53 \times 10^{-5}$ mg/L, zinc sulfate at 0.259 mg/L, fructose at 2000 mg/L, HEPES at 15 mM, putrescine at 0.048 mg/L, thioctic acid at 0.0618 mg/L, sodium pyruvate at 110.03 mg/L, linoleic acid at 0.025 mg/L, l-alanine at 20.173 mg/L, l-asparagine (freebase) at 17.5 mg/L, l-asparagine at 122.01 mg/L, l-aspartic acid at 24.99 mg/L, l-cystine at 63.98 mg/L, l-cysteine at 5.268 mg/L, glutamic acid at 56.9 mg/L, l-glutamine at 600 mg/L, glycine at 23.25 mg/L, l-histidine at 35.69 mg/L, l-isoleucine at 74.68 mg/L, leucine at 77.43 mg/L, l-lysine at 113.16 mg/L, l-methionine at 22.34 mg/L, l-phenylalanine at 47.69 mg/L, l-proline at 38.36 mg/L, l-serine at 32.55 mg/L, l-threonine at 70.07 mg/L, l-tryptophan at 11.81 mg/L, l-tyrosine at 75.17 mg/L, l-valine at 69.31 mg/L, biotin at $1.13 \times 10^{-2}$ mg/L, D-Ca-pantothenate at 2.87 mg/L, choline chloride at 6.99 mg/L, folic acid at 3.2 mg/L, l-inositol at 10.45 mg/L, niacinamide at 2.81 mg/L, pyriodxal at 2.8 mg/L, pyridoxine at $1.85 \times 10^{-2}$ mg/L, riboflavin at 0.291 mg/L, thiamine at 2.9 mg/L, vitamin $B_{12}$ at $4.99 \times 10^{-2}$ mg/L. The pH of this particularly preferred embodiment is 7.2 and the osmolality is 290 mOsm. The concentration of these components can be varied within suitable and preferable ranges according to the teachings of this invention in order to optimize the growth of a particular cell type in culture.

The cell culture media of this invention are desirably supplemented with growth factors, and optimized according to the individual cell type desired to be cultured. Such supplementation and optimization are within the ordinary skill in the art. In some preferred embodiments, the invention is a cell culture medium that may be supplemented with any or all of the following growth factors at the following approximate levels (or within one significant digit): insulin at 10 μg/ml, transferrin at 10 μg/ml, (recombinant human or other source and/or species) epidermal growth factor at 10 ng/ml, somatotropin (porcine or other species) at 0.005 IU/ml, (porcine or other species) pituitary extract at 1 μl/ml, and aprotinin at 10 μg/ml.

In some preferred embodiments, the cell culture media and methods of this invention are particularly well adapted for establishing primary cultures of human fetal cells. In further particularly preferred embodiments, the invention is a method in which the culture medium is utilized in establishing primary cultures of human pancreatic epithelial ductal cells isolated from pancreatic tissue, human prostate epithelial cells isolated from prostate tissue, or human kidney epithelial cells isolated from kidney tissue. In other embodiments, similar methods are used to culture cells isolated from other tissues, such as from the group consisting of tissues of the following biological systems: Central Nervous System: Brain—Cerebrum (gray and white matter containing neurons, glia, etc.) and Brain—Cerebellum, Eye, Brainstem (pons, medulla, midbrain), Spinal Cord; Endocrine: Adrenal (cortex and medulla), Ovary, Pancreas (Islets of Langerhans and exocrine pancreas), Parathyroid, Pituitary (adenohypophysis and neurohypophysis), Testis, Thyroid (follicular epithelium, parafollicular cells, colloid, etc.); Breast: Breast (lobules, ducts, myoepithelial cells, etc.); Hematopoietic: Spleen, Tonsil, Thymus, Bone marrow (lymphocytes, monocytes/macrophages, granulocytes, erythroid precursors, megakaryocytes, mast cells, osteoclasts, osteoblasts), Peripheral blood cells (neutrophils, lymphocytes, monocytes, basophils, eosinophils, red blood cells, platelets); Respiratory: Lung (bronchi, bronchioles, alveoli, etc.); Cardiovascular: Heart, Blood vessels (arteries, veins, etc.); Gastrointestinal: Esophagus, Stomach (fundus), Small intestine (Ileum, jejunum or duodenum), Colon, Liver (portal triads, hepatic cells, etc.), Salivary Gland; Genitourinary: Kidney, Urinary, Bladder, Ureter, Urethra, Fallopian tube, Vagina, Placenta, Prostate, Uterus, Cervix; Musculoskeletal: Skeletal muscle; Skin: Skin (epidermis, appendages, dermis); Peripheral Nerve: Peripheral Nerve; Mesothelial cells: Lining cells from chest wall, abdominal wall, pericardium or from the surface of gastrointestinal, heart and/or lung samples, etc.

In another preferred embodiment, the invention is a cell culture medium that may be supplemented with ethanolamine at a final concentration of 1 μM, phosphoethanolamine at a final concentration of 1 μM, triiodithyronine at a final concentration of 5 pM, selenium at a final concentration of 25 nM, hydrocortisone at a concentration of 1 nM, progesterone at a final concentration of 10 nM, forskolin at a final concentration of 1 μM, and heregulin at a final concentration of 10 nM.

In yet another particularly preferred embodiment, the invention is a cell culture medium that may be supplemented with extracellular matrix factors such as fibronectin or laminin.

In another particularly preferred embodiment, the invention comprises methods in which the culture medium is utilized in the culture of human pancreatic epithelial ductal cells.

In another preferred embodiment, the invention is a method in which the culture media is utilized in establishing primary cultures of human kidney cells, particularly fetal kidney epithelial cells, isolated from fetal kidney tissues.

In another preferred embodiment, invention is a method in which the culture media is utilized in the culture and expansion (two to eight passages) of human fetal kidney epithelial cells.

BRIEF DESCRIPTION OF THE SEVERAL VIEWS OF THE DRAWING(S)

FIG. 1 shows the establishment and culture of human fetal kidney tissue at passage 0 (primary culture), 4, 6, and 7. These cells were grown in I3F medium with growth supplements according to Example 1 herein.

Figure 2:
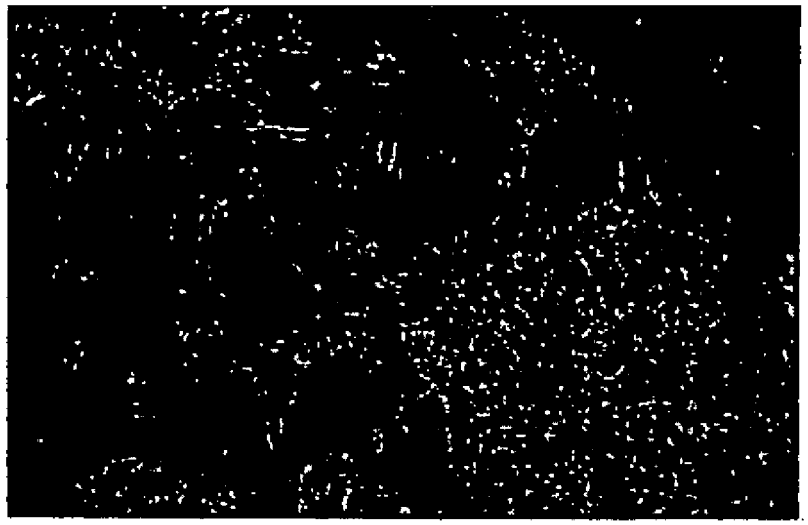
Figure 2:
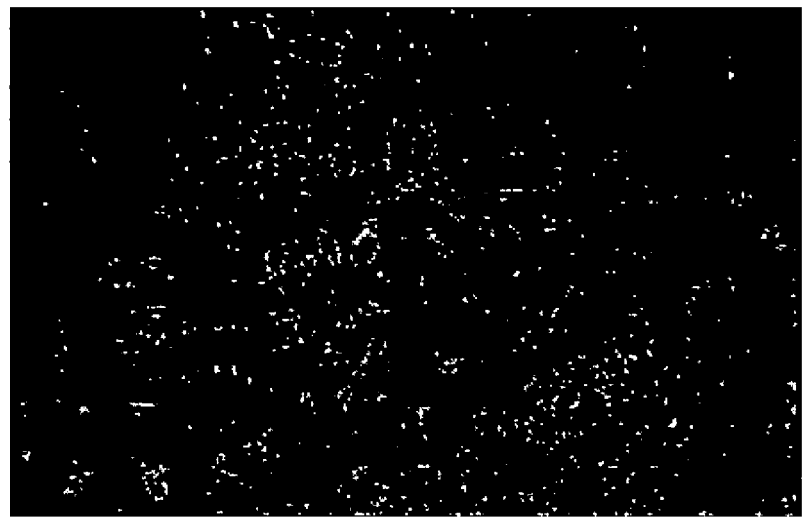
Figure 2:

FIG. 2 shows comparisons of primary cultures of human pancreatic epithelial ductal cells grown in three different media. In panel A, the cells are established in CMRL 1066 medium for three days and cultured in F12:DME (50:50 v/v) medium. In panel B, the cells are established and cultured in I3F medium with the addition of 15 mM glucose. In panel C, the cells are established and cultured in I3F medium.

Figure 3:
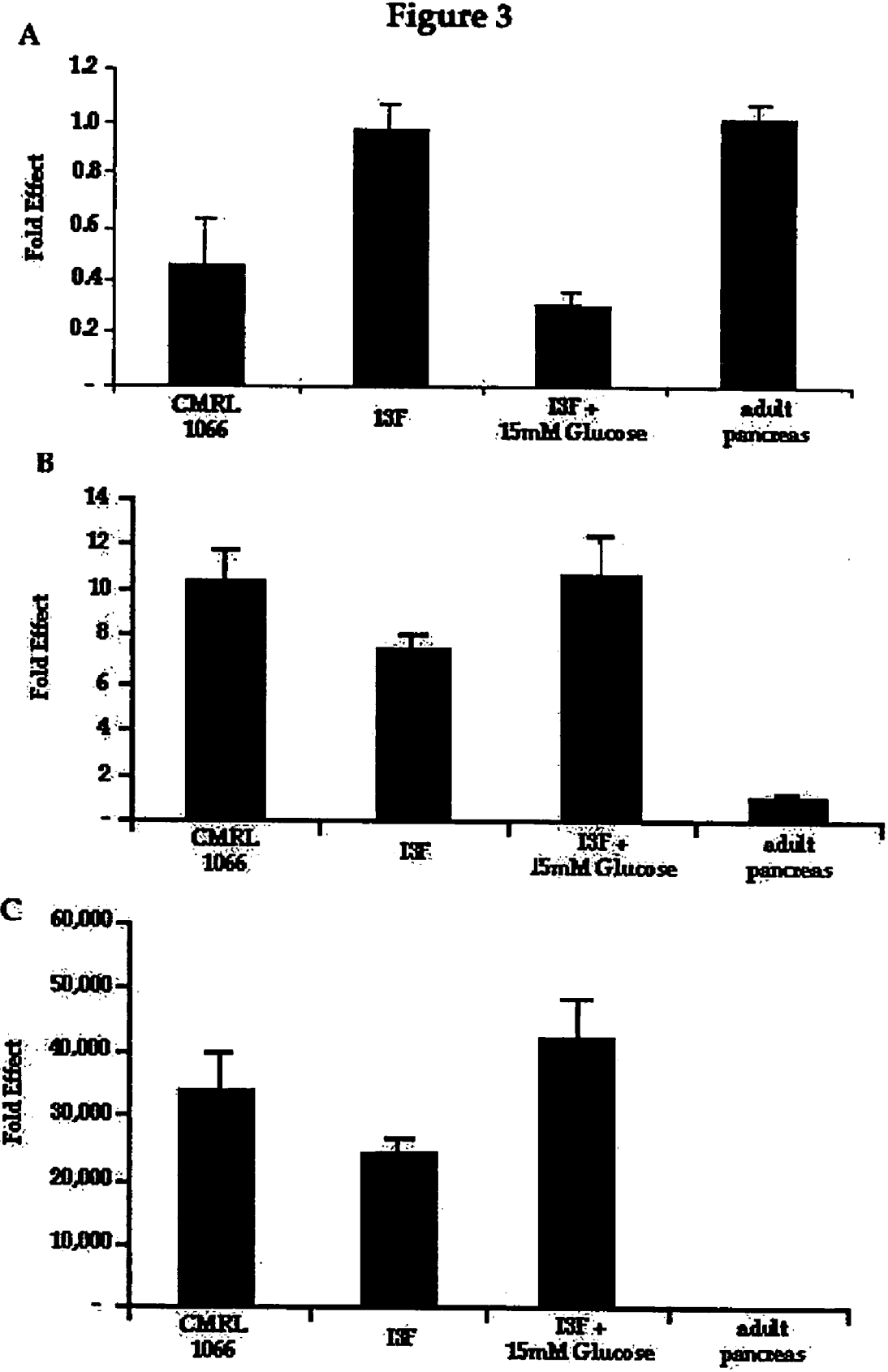

FIG. 3 shows the messenger RNA (mRNA) levels of a fibroblast cell marker (vimentin) and an epithelial cell marker (cytokeratin 19), and the growth rates of primary cultures of human pancreatic epithelial ductal cells. In panel A, vimentin mRNA levels were measured in cells that were established in CMRL 1066 medium for three days and cultured in F12:DME (50:50 v/v) medium, cells that were established and cultured in I3F medium with the addition of 15 mM glucose, and in cells that were established and cultured in I3F medium. As a positive control, commercially purchased adult human pancreatic cDNA (Ambion, Inc., Austin, Tex.) was used and the results are expressed in (−)fold effect when compared to this positive control. In panel B, cytokeratin 19 (ck19) mRNA levels were measured in the same conditions as described in panel A. In panel C, insulin mRNA levels were measured in the same conditions as described in panel A.

DESCRIPTION OF THE PREFERRED EMBODIMENTS

Definitions

The terms "cell culture medium" and "culture medium" refer to the aqueous environment in which vertebrate cells are grown in culture. The medium comprises the physiochemical, nutritional, and hormonal environment. Traditionally the medium has been formulated by the addition of nutritional and growth factors necessary for cell growth or survival.

A "defined medium" refers to a medium comprising nutritional and hormonal requirements necessary for the survival and growth of the cells in culture such that the components of the medium are known. A defined medium provided by the method of this invention establishes a local environment for a particular cell that may differ from the general environment of the medium.

The expression "enhancing survival of a cell" refers to the act of increasing the duration of the viable lifespan of a particular cell in cell culture.

The phrase "enhancing proliferation of a cell" encompasses the step of increasing the rate and/or extent of cell division in cell culture relative to an untreated cell. An increase in cell proliferation in cell culture can be detected by counting the number of cells before and after culturing in the cell culture media disclosed herein. The extent of proliferation can be quantified via microscopic examination of the percentage and number of mitotic figures in the culture and the degree of confluency. Cell proliferation can also be quantified by other commonly used methods.

The term "long-term culture" refers to cells that are capable of survival and growth when placed in a culture medium containing the appropriate nutrients and growth factors without entering into quiescence. In certain preferred embodiments, cells are passaged in "long-term culture" for at least preferably 40, and more preferably 60, cell culture population doublings.

The term "passage" or "split" refers to the sub-culturing of cells or the transfer or transplantation of cells (with or without dilution) from one culture vessel to another with the addition of fresh nutrient mixture.

The term "primary culture" refers to cells that are directly isolated from tissues and dissociated from each other, and that are capable of survival and/or growth when placed in a culture medium containing the appropriate nutrients and growth factors.

The term "quiescence" refers to a state where cells in culture cease to be in a growth phase and stop dividing.

"Serum-free media" refers to a medium lacking animal serum. The hormones, growth factors, transport proteins, attachment factors, peptide hormones and the like typically found in serum which are necessary for the survival or growth of particular cells in culture are typically added as defined supplements to serum-free media.

In vertebrate cell cultures, especially human-derived cell cultures, "senescence" is the property attributable to finite cell cultures, namely, their inability to grow beyond a finite number of population doublings.

Determining the particular component mixture(s) and in turn providing a defined medium required by a particular cell can be accomplished by the artisan of ordinary skill in cell culture. There are several known approaches to determining the requirements for a given cell line. The method of choice will depend on the cell line. Several possibilities are known, variations on methods requiring only the selection of a proper inoculum density and the beginning of testing of various combinations of media components for their growth-promoting effects. Alternatively, if the cells produce a desired product and secrete it into the medium, then the testing may be of various combinations of media components for their effects on secretion level of the desired product.

A nutrient mixture used for growing mammalian cells in culture typically provides at least one component from one or more of the following categories: a carbon or energy source, usually in the form of a carbohydrate such as glucose or glutamine, or other sugars such as sucrose, galactose, mannose, fructose or the like, "essential" and "non-essential" amino acids which provide nitrogen among other things, vitamins at low concentrations which are cofactors in enzyme reactions, other organic compounds that are required at low concentrations such as fats and fat soluble components including fatty acids and phospholipids precursors, trace elements that are defined as inorganic compounds or naturally occurring elements required at low concentrations, usually in the micromolar range, and inorganic salts.

Nutrient supplementation of cell culture media is well known in the art. Examples of commonly used supplements for serum-free culture and their effective concentrations are given in Table 8.2 of Mather and Roberts, Introduction to Cell And Tissue Culture (Plenum Press, 1998). The nutrient mixture of this invention may optionally be supplemented with one or more components according to known methods, such as from the following categories: hormones and other growth factors such as, for example, insulin, testosterone, transferrin, and epidermal growth factor, nucleosides such as adenosine and thymidine, buffers such as HEPES (4-[2-Hydroxethyl]-1-piperazine-ethanesulfonic acid), and extracellular matrix proteins such as fibronectin.

The culture medium can be changed at various intervals (e.g. about every one to five days), and the cells cultured at a physiologically acceptable temperature between about 33 degrees to 38 degrees Celsius, preferably at about 37 degrees Celsius.

Cell culture systems of the present invention comprise a cell culture medium as described herein, and a substrate for the cells such as those commonly in current use or hereafter identified, such as those comprising metal, plastic, polyurethane-type polymers, glass, collagen, gel, hollow fibers, fibronectin, laminin, heparin sulfate proteoglycan, microcarriers composed of or coated with any of the above, or a tissue equivalent. Selection of cell culture systems for use in the present invention are made according to methods commonly known in the art, taking into consideration the shear forces to which the cell culture will be subjected, the gaseous environment, and the particular requirements of the cell and the medium to be provided.

The cell culture media of this invention are particularly well suited for use in tissue culture dishes, tubes, wells, hollow fiber bioreactors, fermentors, spinner flasks, roller bottles and the like.

DETAILED DESCRIPTION OF THE INVENTION

We describe a serum-free cell culture medium containing fructose as the primary carbon energy source. Development of this invention is based part on the discovery that the cell culture media is able to support the establishment and growth of primary cultures derived from a variety of human tissues. In its broadest form, this invention encompasses a mammalian cell culture medium with fructose as the primary carbon source and certain levels of calcium, magnesium, and potassium salts. These inorganic salts and fructose, suitable concentration ranges, and preferred concentration ranges in milligrams per liter (mg/L) are listed in Table 1 below.

TABLE 1

Inorganic Salts and Fructose

| Inorganic Salt | Suitable Conc. (mg/L) | Preferred Conc. (mg/L) |
|---|---|---|
| Calcium Chloride (CaCl$_2$) | 0-270 | 150-200 |
| Potassium Chloride (KCl) | 150-500 | 250-350 |
| Potassium Nitrate (KNO$_3$) | 0.006-0.02 | 0.010-0.015 |
| Magnesium Sulfate (MgSO$_4$)(anhyd) | 30-110 | 40-90 |
| Magnesium Chloride-6HO | 15-60 | 25-40 |
| Fructose | 1000-3000 | 1500-2500 |

For convenience, the solid ingredients of the medium may be combined together, and this mixture may be stored as a single unit.

A variety of inorganic metal salts, commonly called trace elements, are also typically present in this invention at certain levels of concentration. These trace elements and suitable concentration ranges in milligrams per liter (mg/L) are listed in Table 2 below.

TABLE 2

Trace Elements

| Trace element | Suitable Conc. (mg/L) | Preferred Conc. (mg/L) |
|---|---|---|
| Sodium Selenite (NaSeO$_3$-5H$_2$O) | 0.006-0.02- | 0.010-0.015 |
| Ammonium Metavanadate | $1.5 \times 10^{-4}$-$5.3 \times 10^{-4}$ | $2.5 \times 10^{-4}$-$4.0 \times 10^{-4}$ |
| Molybdic Acid-4H$_2$O(ammonium) | $1.5 \times 10^{-3}$-$5.6 \times 10^{-3}$ | $2.5 \times 10^{-3}$-$4.0 \times 10^{-3}$ |
| Cupric Sulfate-5H$_2$O | $3.75 \times 10^{-4}$-$1.2 \times 10^{-3}$ | $5 \times 10^{-4}$-$1.0 \times 10^{-3}$ |
| Ferrous Sulfate-7H$_2$O | 0.1-0.4 | 0.15-0.3 |
| Manganese Sulfate | $2 \times 10^{-5}$-$7 \times 10^{-5}$ | $3.5 \times 10^{-5}$-$5.5 \times 10^{-5}$ |
| Zinc Sulfate-7H$_2$O | 0.1-0.4 | 0.20-0.35 |

For convenience, these trace elements are usually prepared as one concentrated aqueous stock solution, preferably about 10,000 fold greater than the desired final concentration when added to the medium. The concentrations listed in Table 2 are the final concentrations in the culture medium.

All twenty of the essential amino acids and the non-essential amino acid cystine, are also present in the media of this invention at certain levels of concentration. These amino acids and suitable and preferred concentrations in milligrams per liter (mg/L) are listed in Table 3 below.

TABLE 3

Amino Acids

| Amino Acid | Suitable Conc. (mg/L) | Preferred Conc. (mg/L) |
|---|---|---|
| L-Alanine | 10-40 | 15-30 |
| L-Asparagine (freebase) | 8-35 | 15-25 |
| L-Asparagine-H$_2$O | 2-10 | 4-7.5 |
| L-Arginine-HCl | 60-250 | 100-175 |
| L-Aspartic Acid | 10-50 | 20-35 |
| L-Cystine-2HCl | 30-130 | 45-75 |
| L-Cysteine-HCl-H$_2$O | 2-15 | 4-9 |
| L-Glutamic Acid | 20-120 | 45-75 |
| L-Glutamine | 300-1200 | 500-1000 |
| Glycine | 10-50 | 25-40 |
| L-Histidine HCl-H$_2$O | 15-75 | 25-45 |
| L-Isoleucine | 35-150 | 55-100 |
| L-Leucine | 35-155 | 55-100 |
| L-Lysine-HCl | 50-230 | 95-150 |
| L-Methionine | 10-45 | 15-35 |
| L-Phenylalanine | 20-100 | 45-75 |
| L-Proline | 15-80 | 25-65 |
| L-Serine | 15-70 | 25-65 |
| L-Threonine | 35-145 | 50-100 |
| L-Tryptophan | 5-25 | 10-20 |
| L-Tyrosine (disodium salt) | 35-155 | 50-100 |
| L-Valine | 30-140 | 60-110 |

A variety of vitamins are typically also present in this invention at certain levels of concentration. These vitamins and suitable and preferred concentrations in milligrams per liter (mg/L) are listed below in Table 4.

TABLE 4

Vitamins

| Vitamin | Suitable Conc. (mg/L) | Preferred Conc. (mg/L) |
|---|---|---|
| Biotin | $5.6 \times 10^{-3}$-$1.7 \times 10^{-2}$ | $8.5 \times 10^{-3}$-$1.3 \times 10^{-2}$ |
| D-Ca-Pantothenate | 1.4-4.3 | 2.2-3.5 |
| Choline Chloride | 3.4-10.5 | 5.5-8.0 |
| Folic Acid | 1.5-4.8 | 2.5-4.0 |
| I-Inositol | 5-16 | 8-12.5 |
| Niacinamide | 1.0-4.5 | 2.2-3.2 |
| Pyridoxal HCl | 1.0-4.5 | 2.2-3.2 |
| Pyridoxine-HCl | $9.2 \times 10^{-3}$-$2.8 \times 10^{-2}$ | $1.0 \times 10^{-2}$-$2.0 \times 10^{-2}$ |
| Riboflavin | 0.1-0.5 | 0.2-0.4 |
| Thiamine-HCl | 1.4-4.5 | 2.5-3.8 |
| Vitamin B-12 | 0.020-0.075 | 0.035-0.06 |

Another supplement that is used in the practice of this invention is HEPES (4-[2-Hydroxyethyl]-1-piperazine-ethanesulfonic acid) buffer at a suitable concentration from about 5 to 50 mM, preferably 5 to 25 mM, and more preferably at a concentration from about 10-15 mM. Other commonly known organic buffers may be used in the practice of this invention.

Other organic supplements are used in this invention at certain levels of concentration. These supplements and their suitable and preferred concentrations in milligrams per liter (mg/L) are listed in Table 5 below.

TABLE 5

Other Supplements

| Misc. supplements | Suitable Conc. (mg/L) | Preferred Conc. (mg/L) |
|---|---|---|
| Putrescine-2HCl | 0.02-0.08 | 0.03-0.065 |
| Thioctic Acid | 0.03-0.10 | 0.05-0.08 |
| Sodium Pyruvate | 55-165 | 90-140 |
| Linoleic Acid | 0.01-0.04 | 0.01-0.03 |

The cell culture media of this invention may contain some or all of the components listed in Tables 1 through 5.

For some applications, the cell culture medium is desirably supplemented with growth hormones such as insulin at a final concentration of 0.1-100 µg/ml and preferably 10 µg/ml, transferrin at a final concentration of 0.1-100 µg/ml and preferably of 10 µg/ml, somatotropin (porcine or other species) at a final concentration of 0.0005-0.05 IU/ml and preferably of 0.005 IU/ml, porcine (or other species) pituitary extract at a final concentration of 0.1-10 µg/ml and preferably of 1 µl/ml, and aprotinin at a final concentration of 0.5-100 µg/ml and preferably of 10 µg/ml. In addition to these growth factors, the cell culture medium may, for some preferred applications, contain (recombinant human or other species or source) epidermal growth factor at a final concentration of 0.1-100 ng/ml and preferably 10 ng/ml.

In another preferred embodiment, the cell culture medium is desirably supplemented with fibronectin at a final concentration of 0.1-50 µg/ml and preferably of 5 µg/ml.

In other preferred embodiments, the cell culture medium is desirably supplemented with ethanolamine at a final concentration of 0.1-10 µM and preferably of 1 µM, phosphoethanolamine at a final concentration of 0.1-10 µM and preferably of 1 µM, triiodithyronine at a final concentration of 1-25 pM and preferably of 5 pM, selenium at a final concentration of 1-100 nM and preferably of 25 nM, hydrocortisone at a final concentration of 0.1-50 nM and preferably of 1 nM, forskolin at a final concentration of 0.1-50 µM and preferably of 1 µM, and heregulin at a final concentration of 0.1-50 µM and preferably of 10 nM.

The cell culture media of this invention preferably have fructose as their essential energy source, in combination with a selection of at least one additional component selected from the substituents provided herein, and are tailored to optimize the growth of the particular cells or cell lines desired.

Preparation of Media

The preparation of this cell culture media of this invention will employ conventional methods well known in the art. Following a preferred method, rinse the vessel to be used for preparation of the medium twice with purified water and cover the vessel with aluminum foil to keep out the light. Fill the vessel with purified water to a volume that is less than the desired final volume that will permit sufficient incorporation of solid and other ingredients. A convenient and satisfactory volume is ten to 25 percent (10- to 25-%) less than the final desired volume. Multiply the desired g/L of each component by number of liters needed to get the amount in grams of that component that will be added. Weigh out the necessary amount of each of the solid ingredients. The solid ingredients included here are considered to be the amino acids, vitamins, fructose and inorganic salts such as calcium salts, potassium salts, magnesium salts, sodium salts, ammonium salts, copper salts, iron salts, manganese salts and zinc salts. For convenience, the solids can be mixed together and added to the purified water in one step.

After the addition of the sodium bicarbonate, let the media mix for fifteen to twenty (15-20) minutes. The pH is then checked and should be between 6.5 and 7.2. The pH should then be adjusted to 7.20 preferably using sodium hydroxide (NaOH), either in liquid (10M) or solid form (although other means for pH adjustment are encompassed in this invention). When the pH is adjusted, add the HEPES and let the media mix fifteen to twenty (15-20) minutes. Adjust the osmolality (a measure of the total dissolved solids in the medium, measured in the number of osmoles per liter) to the proper level. A satisfactory range would be 290-325 mOsm. The osmolality can be conveniently checked using an osmometer. Using an osmometer with 100 mOsm and 500 mOsm standards in duplicate, check three (3) samples of the media. Average the three (3) samples and calculate the amount of salt needed to bring the osmolality to the desired level.

Example: If the desired osmolality is 290 mOsm and the average of the three readings is 82.33, the calculation preferably used according to this invention for the amount of salt (sodium chloride or any other suitable salt) needed to achieve the desired osmolality would be as follows:

Subtract the average of the three readings from the desired osmolality.

Multiply the result by a fixed multiplier, in this example, 0.031

Multiply the result by the desired end volume

The result is the amount of salt (NaCl) in grams that is needed in order to achieve the desired osmolality.

For a desired final volume of forty (40) liters, the calculation for a preferred embodiment of this invention is:

$$290-82.33=207.67 \times 0.031=6.437 \text{ g/L} \times 40 \text{ liters}=257.51 \text{ grams of NaCl}.$$

Add the salt and let the medium mix for thirty to forty-five (30-45) minutes and, again, check three (3) samples of the media. The media should be at the desired osmolality level.

In a culture hood, sterile filter (preferably 0.22 µm filter or finer) the media into glass media bottles or other suitable container for storage.

All of the cell culture media of this invention may be formulated and packaged as a dry or concentrated preparation for reconstitution prior to use. In preferred embodiments of this invention, the medium is prepared as a dry powder containing all or some of the media components. For convenience, each ingredient may be weighed out in a predetermined amount, and subgroups of components (such as the salts or amino acids, for example) can be combined together and stored as the amino acid supplement mixture. Any remaining components may then be added when the dry medium is reconstituted. Reconstitution may be done just prior to use. Alternatively, the medium may be reconstituted and packaged. The shelf life of this medium as a dry powder stored at about 4 degrees C. is at least several years. The liquid medium, either as prepared or as reconstituted from the dry powers is less stable, but when stored at about 4 degrees C., preferably in the dark, is stable for about six weeks to two months or longer.

Reconstitution may be performed by adding concentrated stocks of bicarbonate, base of other of the medium components, so long as the relative concentrations described herein are present. If those components are added as solids, reconstitution is accomplished by the addition of sterile, de-ionized, purified or other tissue culture grade water. The medium is sterilized prior to use, according to known methods.

The above steps constitute the preparation of the basic medium of this invention. Antibiotics, preferably gentamycin (at 50-150 µg/ml) and/or penicillin (at 5-10 U/ml)-streptomycin (at 5-10 µg/ml) may be added if deemed necessary. After filtration, additional supplements, including, for example, trace elements or growth factors may be added to the media. The trace elements are preferably prepared as a stock solution and added to achieve the desired final concentration. The growth factors should be added preferably just before using the media to the desired final concentration. In some embodiments, other sugars can be used to supplement the media of this invention. The sugars commonly include but are not limited to, glucose, sucrose, and galactose.

Use of the Media, Methods, and Cells

The media of this invention are particularly useful for the primary culture of human cells from a variety of tissues. Culturing tissue preparations in these media is suitable for, and frequently may result in, the establishment of a primary culture that is predominantly epithelial cells that can be used to establish a long-term culture. These cells tend to establish quickly, can be subcultured for more passages, and have a faster population doubling time when compared to cells established in the currently publicly available media.

Cells cultured according to the methods of this invention may be obtained from tissue sources as described herein, or may be themselves cells previously in culture. Cells may be transformed or non-transformed, or immortalized according to other methods commonly practiced in the art.

For cells to be produced from tissue, cells are typically prepared by mincing a tissue that comprises the cells, thereby obtaining a substructure of the tissue or free cells, then concentrating the substructures or cells, resuspending the concentrated substructures or cells in a culture medium of this invention that is capable of supporting sustained cell division, incubating the culture, and passaging the culture periodically. The present invention further provides a method of preparing clonal strains, which method comprises the steps of preparing a cell culture as described above, growing the culture into a confluent layer of cells, dissociating the cells, inoculating the cells into another culture vessel that contains a conditioned medium of this invention for a first plating, harvesting individual colonies of cells, inoculating the colonies into another culture vessel for a second plating, and passaging the resultant cells periodically.

This invention provides expanded cell cultures prepared using the methods taught herein, and methods of using such cell cultures in diagnostic assays, in therapeutic treatments, and for the production of desired protein products.

For use in cell culture, the medium of this invention is typically inoculated with the selected cells. Preferably, the inoculum volume will be on the order of about one-fifth (or less) of the volume of the medium, although some variation from this inoculum volume may be made according to commonly known methods. After inoculation, the cell culture is maintained in an appropriate environment, taking into consideration such factors as temperature, light, oxygen and carbon dioxide concentration.

The prepared medium may be used for the culture of various mammalian cells. In the case of primary cultures, the enzyme-digested tissues are treated to neutralize the enzymes and/or extensively washed to remove them, resuspended in the medium and are then plated onto culture plates. In the case of continuous cell culture, the cells are typically resuspended at the desired concentration in the medium and are removed from the plate, washed and then plated onto culture plates. In a certain preferred method, the culture plates are pre-coated with basement membrane proteins such as fibronectin to ensure proper adhesion.

The resulting cell populations may be expanded and harvested for use in a variety of biological assays. Additionally, the cells may be cultured long-term and, according to the practice of this invention, may result in a cell line that can be passaged for a desired period of time, with a significant expansion of the cell population (10- to 1000-fold). Alternatively, the culture medium itself may be collected and assayed for proteins or other organic compounds secreted by the cells.

The media of this invention may be used for culturing cells in a variety of cell culture systems as described above. Such systems are used for culturing cells as a monolayer, or preferably, for culturing the cells in suspension. The cells may be grown as a small-scale culture, i.e. in volumes of about two (2) liters or less. Alternatively, and preferably in certain embodiments, the cells are cultured in large volumes such as up to about sixteen liters in spinner flasks or about 80 liters or more in fermentors designed for commercial production of biological compounds from animal cells.

The cells themselves or a biological compound inside of the cells may be the desired end product of the culturing. If so, they may be harvested and separated from the culture medium. The cells grown and recovered according to the teachings of this invention are suitable for delivery to an individual in need of growth of such cells within them, such as for regrowth of damaged or diseased tissue, or as in vivo systems for the delivery of a cell product. The methods of this invention also can be used to enhance survival and/or proliferation of desired cells derived from an individual, this facilitating autologous transplants into the individual. Alternatively, a protein or other organic compound secreted by the cells into the medium may be the desired end product of the culturing. In this situation, the medium may be separated from the cells, and the compound of interest can then be purified from the medium.

Selected Preferred Embodiments

In certain preferred embodiments, the invention comprises a composition of serum-free cell culture medium having a primary energy source consisting essentially of fructose present at a concentration of from 3000 mg/L to 1000 mg/L.

In another embodiment, the culture medium composition consists of the following inorganic salts at the indicated range of concentrations: calcium chloride at a concentration of from 270 mg/L to 0 mg/L, potassium chloride at a concentration of from 500 mg/L to 150 mg/L, potassium nitrate at a concentration of from 0.02 mg/L to 0.006 mg/L, magnesium sulfate (anhydrous) at a concentration of from 110 mg/L to 30 mg/L, and magnesium chloride at a concentration of from 60 mg/L to 15 mg/L.

In another embodiment, the composition of the culture medium consists of the following inorganic salts at the indicated range of concentrations: calcium chloride at a concentration of from 270 mg/L to 0 mg/L, potassium chloride at a concentration of from 500 mg/L to 150 mg/L, potassium nitrate at a concentration of from 0.02 mg/L to 0.006 mg/L, magnesium sulfate (anhydrous) at a concentration of from 110 mg/L to 30 mg/L, and magnesium chloride at a concentration of from 60 mg/L to 15 mg/L.

In certain of these and other embodiments, the compositions of this invention comprise a cell culture medium consisting of the following inorganic metal salts, commonly called trace elements, at the indicated range of concentrations: sodium selenite at a concentration of from 0.02 mg/L to 0.006 mg/L, ammonium metavanadate at a concentration of from $5.3 \times 10^{-4}$ mg/L to $1.5 \times 10^{-4}$ mg/L, molybdic acid (ammonium) at a concentration of from $5.6 \times 10^{-3}$ mg/L to $1.5 \times 10^{-3}$ mg/L, cupric sulfate at a concentration of from $1.2 \times 10^{-3}$ mg/L to $3.75 \times 10^{-4}$ mg/L, ferrous sulfate at a concentration of from 0.4 mg/L to 0.1 mg/L, manganese sulfate at a concentration of from $7 \times 10^{-5}$ mg/L to $2 \times 10^{-5}$ mg/L, and zinc sulfate at a concentration of from 0.4 mg/L to 0.1 mg/L.

In yet other embodiments, the culture medium of this invention consists of the following amino acids at the indicated range of concentrations: l-alanine at a concentration of from 40 mg/L to 10 mg/L, l-asparagine (freebase) at a concentration of from 35 mg/L to 8 mg/L, l-asparagine-$H_2O$ at a concentration of from 10 mg/L to 2 mg/L, l-arginine at a concentration of from 250 mg/L to 60 mg/L, l-aspartic acid at a concentration of from 50 mg/L to 10 mg/L, l-cystine at a concentration of from 130 mg/L to 30 mg/L, l-glutamic acid at a concentration of from 120 mg/L to 20 mg/L, l-glutamine at a concentration of from 1200 mg/L to 300 mg/L, glycine at a concentration of from 50 mg/L to 10 mg/L, l-histidine at a concentration of from 75 mg/L to 15 mg/L, l-isoleucine at a concentration of from 150 mg/L to 35 mg/L, l-leucine at a concentration of from 155 mg/L to 35 mg/L, l-lysine at a concentration of from 230 mg/L to 50 mg/L, l-methionine at a concentration of from 45 mg/L to 10 mg/L, l-phenylalanine at a concentration of from 100 mg/L to 20 mg/L, l-proline at a concentration of from 80 mg/L to 15 mg/L, l-serine at a concentration of from 70 mg/L to 15 mg/L, l-threonine at a concentration of from 145 mg/L to 35 mg/L, l-tryptophan at a concentration of from 25 mg/L to 5 mg/L, l-tyrosine at a concentration of from 155 mg/L to 35 mg/L, and l-valine at a concentration of from 140 mg/L to 30 mg/L.

In still other embodiments, this invention provides culture medium consisting of the following vitamins at the indicated range of concentrations: biotin of from $1.7 \times 10^{-2}$ mg/L to $5.6 \times 10^{-3}$ mg/L, D-Ca-pantothenate of from 4.3 mg/L to 1.4 mg/L, choline chloride of from 10.5 mg/L to 3.4 mg/L, folic acid of from 4.8 mg/L to 1.5 mg/L, l-inositol of from 16 mg/L to 5 mg/L, niacinamide of from 4.5 mg/L to 1 mg/L, pyriodxal of from 4.5 mg/L to 1 mg/L, pyridoxine of from $2.8 \times 10^{-2}$ mg/L to $9.2 \times 10^{-3}$ mg/L, thiamine of from 4.5 mg/L to 1.4 mg/L, and vitamin B-12 of from 0.075 mg/L to 0.02 mg/L.

In certain of these embodiments, the culture medium consists of the following miscellaneous components at the indicated range of concentrations: HEPES at a concentration of 10-15 mL/L (v/v), putrescine at a concentration of from 0.08 mg/L to 0.02 mg/L, thioctic acid at a concentration of from 0.1 mg/L to 0.03 mg/L, sodium pyruvate at a concentration of from 165 mg/L to 55 mg/L, linoleic acid at a concentration of from 0.04 mg/L to 0.01 mg/L, and l-cysteine at a concentration of from 15 mg/L to 2 mg/L.

In certain preferred embodiments, the culture medium consists of the following components at the indicated range of concentrations:

| Component | Concentration (mg/L) |
|---|---|
| Inorganic Salts: | |
| Calcium Chloride (CaCl$_2$) | 0-270 |
| Potassium Chloride (KCl) | 150-500 |
| Potassium Nitrate (KNO$_3$) | 0.006-0.02 |
| Magnesium Sulfate (MgSO$_4$)(anhyd) | 30-110 |
| Magnesium Chloride-6H$_2$O | 15-60 |
| Sodium Chloride (NaCl) | 3100-9300 |
| Sodium Bicarbonate (NaHCO$_3$) | 600-1800 |
| Sodium Phosphate (NaH$_2$PO$_4$—H$_2$O) | 20-70 |
| Sodium Phosphate dibasic (Na$_2$HPO$_4$) | 40-150 |
| Sodium Selenite (NaSeO$_3$-5H$_2$O) | 0.006-0.02 |
| Ammonium Metavanadate | $1.5 \times 10^{-4}$-$5.3 \times 10^{-4}$ |
| Molybdic Acid-4H$_2$O(ammonium) | $1.5 \times 10^{-3}$-$5.6 \times 10^{-3}$ |
| Cupric Sulfate-5H$_2$O | $3.75 \times 10^{-4}$-$1.2 \times 10^{-3}$ |
| Ferrous Sulfate-7H$_2$O | 0.1-0.4 |
| Manganese Sulfate | $2 \times 10^{-5}$-$7 \times 10^{-5}$ |
| Zinc Sulfate-7H$_2$O | 0.1-0.4 |
| Other Components: | |
| Fructose | 1000-3000 |
| HEPES | 10-15 mL/L (v/v) |
| Putrescine-2HCl | 0.02-0.08 |
| Thioctic Acid | 0.03-0.1 |
| Sodium Pyruvate | 55-165 |
| Linoleic Acid | 0.01-0.04 |
| Amino Acids: | |
| L-Alanine | 10-40 |
| L-Asparagine (freebase) | 8-35 |
| L-Asparagine-H$_2$O | 2-10 |
| L-Arginine-HCl | 60-250 |
| L-Aspartic Acid | 10-50 |
| L-Cystine-2HCl | 30-130 |
| L-Cysteine-HCl-H$_2$O | 2-15 |
| L-Glutamic Acid | 20-120 |
| L-Glutamine | 300-1200 |
| Glycine | 10-50 |
| L-Histidine HCl-H$_2$O | 15-75 |
| L-Isoleucine | 35-150 |
| L-Leucine | 35-155 |
| L-Lysine-HCl | 50-230 |
| L-Methionine | 10-45 |
| L-Phenylalanine | 20-100 |
| L-Proline | 15-80 |
| L-Serine | 15-70 |
| L-Threonine | 35-145 |
| L-Tryptophan | 5-25 |
| L-Tyrosine (disodium salt) | 35-155 |
| L-Valine | 30-140 |
| Vitamins: | |
| Biotin | $5.6 \times 10^{-3}$-$1.7 \times 10^{-2}$ |
| D-Ca-Pantothenate | 1.4-4.3 |
| Choline Chloride | 3.4-10.5 |
| Folic Acid | 1.5-4.8 |
| I-Inositol | 5-16 |
| Niacinamide | 1.0-4.5 |
| Pyridoxal-HCl | 1.0-4.5 |
| Pyridoxine-HCl | $9.2 \times 10^{-3}$-$2.8 \times 10^{-2}$ |
| Riboflavin | 0.10-0.5 |
| Thiamine-HCl | 1.4-4.5 |
| Vitamin B12 | 0.020-0.075 |
| pH | 7.2 |
| Osmolality (mOsm) | 290-325 |

In particularly preferred embodiments of this invention, the primary energy source is fructose and the culture medium is free of animal serum.

The following examples illustrate preferred modes for practicing this invention, but should not be construed to limit the use of the invention to just these examples.

EXAMPLES

Example 1

Growth of Human Kidney Cells in Culture

To obtain primary human kidney cells from kidney tissue, and to grow them in sustainable cell culture, the following exemplary method is described. Prepare the media of this invention with or without gentamycin and/or pencillin-streptomycin at the desired concentration. Transfer kidneys or kidney tissue from a human or animal subject to this wash medium. Remove outer membranes of kidney with forceps. Dip kidneys briefly in seventy percent (70%) ethanol and transfer to fresh wash medium. Transfer kidneys to a fresh sterile Petri dish and mince with curved scissors. Resuspend tissue in 10 ml wash medium and pellet in a centrifuge at 1200 rpm for 4 minutes. The tissue pieces are desirably resuspended in the media of this invention containing collagenase/dispase (0.01-0.2%) overnight or for approximately twenty-four hours. Remove the wash medium and repeat this wash step with another 10 ml of fresh wash medium. Remove the wash medium and resuspend the cell pellet in seven milliliters (7 ml) of the media of this invention supplemented with insulin, transferrin, epidermal growth factor, somatotropin, porcine pituitary extract, aprotinin, and gentamycin (this particular embodiment will be referred to herein as "growth medium"). The growth medium is further supplemented with fibronectin at a concentration of 5 µg/ml in the initial plating of the cells.

Distribute the cell suspension evenly into 10 cm sterile culture dishes. Twenty-four hours (24 hours) after plating, add three milliliters of growth medium to the culture. Change the growth medium every two to three days (2-3 days) with fresh growth medium. The resulting primary cell culture of kidney epithelial cells can be passaged every 10 days (or as needed) onto 10 cm plates that are pre-coated with fibronectin at a concentration of 5 µg/ml.

This protocol is suitable for a variety of mammalian kidney tissues including, but not limited to murine, rat, pig, human and fetal human.

The results of this protocol performed with human fetal kidneys are shown in FIG. 1. The top left hand panel shows the cells at primary culture. The top right hand panel shows the cells at passage number four. The bottom left hand panel shows the cells at passage number six. The bottom right hand panel shows the cells at passage number seven. A large percentage of cells at this stage are quiescent and have stopped proliferating.

Example 2

Growth of Human Fetal Kidney Cells

Human fetal kidneys of gestational age between 10 to 18 weeks were obtained from Advanced Biosciences Research (Alameda County, California). Kidneys were procured and shipped to the lab in tissue culture medium on wet ice. Immediately upon arrival, the kidneys were transferred to wash medium (cold PBS containing penicillin/streptomycin and gentamycin). The outer membranes were removed with forceps and the kidneys were briefly washed in 70% ethanol then rinsed twice in wash medium. The kidneys were minced into 1 mm cubes with surgical scissors in a 100 mm dry culture dish. The tissue pieces were plated in 10 ml of a defined serum-free medium referred to herein as "I/3F" or "I3F".

The medium used for this example contained the following components: calcium chloride ($CaCl_2$) at 0.18 g/L, potassium chloride (KCl) at 0.298 g/L, potassium nitrate ($KNO_3$) at 0.000012629 g/L, magnesium sulfate ($MgSO_4$)(anhyd) at 0.068 g/L, magnesium chloride-$6H_2O$ at 0.037 g/L, sodium chloride (NaCl) at 6.2 g/L, sodium bicarbonate ($NaHCO_3$) at 1.2 g/L, sodium phosphate ($NaH_2PO_4$—$H_2O$) at 0.043 g/L, sodium phosphate dibasic ($Na_2HPO_4$) at 0.088 g/L, sodium selenite ($NaSeO_3$-$5H_2O$) at 0.000012629 g/L, ammonium metavanadate at 0.000000351 g/L, molybdic acid-$4H_2O$ (ammonium) at 0.00000372 g/L, cupric sulfate-$5H_2O$ at 0.00000075 g/L, ferrous sulfate-$7H_2O$ at 0.0002502 g/L, manganese sulfate at 4.53E-08 g/L, zinc sulfate-$7H_2O$ at 0.0002589 g/L, fructose at 2 g/L, Hepes at 3.57 g/L, putrescine-2HCl at 0.0000483 g/L, thioctic acid at 0.0000618 g/L, sodium pyruvate at 0.11003 g/L, linoleic acid at 0.00002523 g/L, L-alanine at 0.020173 g/L, L-asparagine (freebase) at 0.0175 g/L, L-asparagine-$H_2O$ at 0.0045 g/L, L-arginine-HCl at 0.12201 g/L, L-aspartic acid at 0.024993 g/L, L-cystine-2HCl at 0.06398 g/L, L-cysteine-HCl-$H_2O$ at 0.005268 g/L, L-glutamic acid at 0.056913 g/L, L-glutamine at 0.6 g/L, glycine at 0.023253 g/L, L-histidine HCl-$H_2O$ at 0.035691 g/L, L-isoleucine at 0.074682 g/L, L-leucine at 0.077436 g/L, L-lysine-HCl at 0.113162 g/L, L-methionine at 0.022344 g/L, L-phenylalanine at 0.047688 g/L, L-proline at 0.038359 g/L, L-serine at 0.032553 g/L, L-threonine at 0.070073 g/L, L-tryptophan at 0.011812 g/L, L-tyrosine (disodium salt) a 0.0751688 g/L, L-valine 0.069316 g/L, biotin at 0.000011299 g/L, D-Ca pantothenate at 0.0028714 g/L, choline chloride at 0.006988 g/L, folic acid at 0.0031972 g/L, l-inositol at 0.010446 g/L, niacinamide at 0.00281098 g/L, Pyridoxal HCl at 0.0028 g/L, pyridoxine-HCl at 0.00001851 g/L, riboflavin at 0.00029128 g/L, thiamine HCL at 0.0029011 g/L, vitamin B12 at 0.0000499 g/L, pH at 7.2, osmolality at 295 mM.

The tissue pieces were transferred into a 15 ml centrifuge tube and the tissue pieces were centrifuged at 1000×g for 5 minutes. The tissue pieces were resuspended in I3F medium containing insulin (10 ug/ml), transferrin (10 ug/ml), epidermal growth factor (20 ng/ml), somatotropin (0.005 IU/ml), pig pituitary extract (0.2%), chicken serum (0.1%), gentamycin (100 ug/ml), penicillin/streptomycin (1×) and collagenase/dispase (0.1%) and incubated at 4° C. overnight. The following day, centrifuge the digested tissue pieces were centrifuged at 1000×g for 5 minutes and washed twice with I3F medium. The pellet was resuspended in 10 ml I3F medium containing insulin (10 ug/ml), transferrin (10 ug/ml), epidermal growth factor (20 ng/ml), somatotropin (0.005 IU/ml), pig pituitary extract (0.2%) and chicken serum (0.1%) and cultured in fibronectin-precoated 10 cm plates.

Under these culture conditions, the human fetal kidney cells attached to the substrate-coated plates and grew as a monolayer. Culture medium was changed twice weekly.

To harvest the cells, the cell monolayers were rinsed once with calcium- and magnesium-free Hanks basic salt solution, incubated in 10 mM EDTA in Hanks basic salt solution at 37 degrees Celsius for 15 minutes. The cells were detached from the culture surface by gentle pipetting. The cell suspension was pelleted by centrifugation at 1000×g for 5 minutes. The supernatant was removed and cells were resuspended in serum-free medium (I3F medium) with non-denaturing adjuvant as appropriate.

Example 3

A Novel Method for Expansion and Differentiation of Human Pancreatic Ductal Cells into Insulin Producing-Cells One of the limiting factors for the progression of islet cell transplantation remains the sufficient supply of insulin-producing cells. We investigated a cell culture model to improve β-cells differentiation in vitro starting from human progenitor pancreatic cells. As will be described more fully below, human pancreatic epithelial ductal cells (hPED), were isolated and then maintained in a defined serum-free "ductal medium" (DM). This specific medium allows these cells to rapidly divide and form a homogeneous epithelial monolayer. However these defined conditions do not support the growth of insulin-secreting β-cells. In order to promote their differentiation into β-cells, we developed a second serum-free defined "islet medium" (IM). The effect of a transfer from DM to IM on hPED cells was initially followed by real-time RT-PCR using the comparative Ct method to examine insulin mRNA level. Interestingly after a 7-day incubation in the IM medium, changes in the insulin transcript level were observed. There was a significant increase in the level of insulin transcripts in HPED cells maintained in the IM compared those in the DM (about 15-20-fold). Additionally, to extend this initial observation we measured C-peptide secretion in culture using a human specific C-peptide Elisa. The C-peptide protein level per cell was significantly higher in conditions where cells were cultured in IM medium and formed aggregates (about 10 fold).

The study presented in this Example validates a two-step serum-free process that utilizes one medium (DM) for the expansion of the undifferentiated population and a second medium (IM) that promotes and supports insulin-secreting cells. The cells produced according to these methods using the media of this invention generate significant numbers of insulin-secreting cells that are suitable for islet transplantation. Such cells are also useful for facilitating the restoration of normoglycemia in a diabetic individual.

We removed all extra connective tissues attached to the human fetal pancreases (13-24 week gestational) by microdissection. The tissue was minced into 0.5 mm³ to 1-mm³ pieces. The minced pancreas pieces were then subjected to enzymatic digestion for twenty (20) minutes at 37 degrees Celsius in a digestion mixture containing the following components at 1 microgram per ml (μg/ml) each dissolved in phosphate buffered saline (PBS): type 4 collagenase (Worthington Biochemical Corporation), soybean trypsin inhibitor ("STI") (Sigma), and hyaluronidase (Sigma). After the digestion period, the tissue mixture was triturated with a pipette to achieve an even suspension of the cells. The cells were then washed by centrifugation at 900 rpm for 15 minutes through a 5% bovine serum albumin (BSA) gradient. This gradient was comprised of 5% (w/v) tissue culture grade BSA that is dissolved in any suitable commercially available tissue culture media, or the media taught in this invention. A suitable example of tissue culture media would be F12:DME (50:50). The cell volume and gradient volume was preferably at a 1:1 ratio.

The supernatant was discarded and the cell pellet resuspended in the media of this invention supplemented with the following growth factors at the indicated final concentrations: recombinant human insulin (rhinsulin) at 10 μg/ml, transferrin at 10 μg/ml, epidermal growth factor (EGF) at 5 ng/ml, ethanolamine at 1 μM concentration, phosphoethanolamine at 1 μM concentration, triiodithyronine at 5 pM concentration, selenium at 25 nM concentration, hydrocortisone at 1 nM concentration, progesterone at 10 nM concentration, forskolin at 1 μM concentration, heregulin at 10 nM concentration, porcine pituitary extract at 5 μl/ml or 75 μg/ml protein concentration, and aprotinin at 25 μg/ml.

The resuspended cells were distributed evenly in fibronectin precoated 24-well sterile tissue culture plates. The 24-well tissue culture plates were precoated with a solution of 5 μg/ml fibronectin diluted in the media of this invention. The tissue culture plates were precoated at least thirty (30) minutes prior to use. Cells extracted from pancreati between thirteen and sixteen weeks gestational stage were distributed evenly into six wells of a 24-well tissue culture plate. Cells extracted from pancreati between seventeen to twenty-four weeks gestational stage were distributed evenly into twelve wells of a 24-well tissue culture plate. Because this particularly preferred embodiment of the media of this invention does not contain any antibiotics or anti-fungal agents, the cells were plated in distinct wells in order to minimize general contamination of the entire primary culture preparation.

Under the above culture conditions, pancreatic ductal cells and some contaminating mesenchymal cells attached onto the plate surface within twenty-four (24) hours. The cells began to spread and divide, ultimately forming a monolayer-type cell culture. The cultures reached approximately seventy-five percent (75%) confluency after seven to ten days in culture and were now suitable for subculturing or passaging at a 1:2 ratio split. The medium was removed from the cells and set aside. This medium will be referred to as "conditioned" medium. The cells were then washed with PBS and dissociated with a collagenase/dispase solution, optionally with STI, at 37 degrees Celsius for approximately 15 minutes. (In some embodiments, this dissociation step may be omitted.) The cells were then washed on a 5% BSA gradient as described above and pooled into a larger cell culture vessel, such as a 100 mm sterile culture dish. The cell culture medium was changed every two to three days using 1:3 ratio of "conditioned" medium to fresh medium. It is recommended to pass the medium through a 0.2-micron filter to remove any cells or particulate matter prior to its reintroduction to a cell culture, although other commonly known methods for purifying or clarifying the medium may be employed according to the teachings of this invention. Filtered conditioned media of this invention may be stored at about four to six degrees Celsius for approximately four to six to eight weeks before re-use. The cells can be subcultured typically after they reach 75% confluency, but they may be subcultured earlier or later, or used in biological assays at any desired confluency.

The results of performing this protocol in three different culture media are shown in FIG. 2. The first panel shows the human fetal pancreatic ductal primary established in the commercially available medium CMRL 1066 (Connaught Medical Research Labs) for three days and then cultured in F:12-DME (50:50) medium supplemented with the growth factors listed above. The second panel shows the same cell preparation cultured in the media of this invention with the growth factors supplement and the addition of glucose at a final concentration of 15 mM. The third panel shows the same cell preparation cultured in the media of this invention supplemented with the growth factors listed above. Morphologically, the third panel shows a more uniform population of epithelial-like cells. The first and second panel shows "islands" of epithelial-like cells along with contaminating mesenchymal cells that are morphologically fibroblast-like in nature.

In order to verify that the cell population achieved by culturing the cells in the media of the invention contains more pancreatic ductal cells, messenger RNA (mRNA) levels of cytokeratin 19 and vimentin were measured. This can be done using any method well known in the art that can quantify mRNA levels. In this particular example, relative quantitative real-time reverse transcription-polymerase chain reaction (RT-PCR) analysis was performed using an ABI PRISM 7700 and 7000 Sequence Detection System instrument and software as previously described in Gibson et al. (*Genome Research* 6(10): 995-1001, 1996).

The results from the mRNA analysis are shown in FIG. 3. In panel A, the results of cytokeratin 19 mRNA analysis on primary cell cultures prepared in (a) commercially available CMRL 1066 and then F:12-DME medium as described above, (b) the media of this invention, and (c) the media of this invention with the addition of glucose at a final concentration of 15 mM are shown. Cytokeratin 19 is an epithelial cell marker that is commonly used in the art (see, e.g., Bouwens et al., *Diabetes* 43(11):1279-83 (November 1994)). Cells that were cultured in the media of this invention had an approximate 24-fold increase in cytokeratin 19 mRNA expression as compared to the internal standard. This increase in mRNA expression is approximately double the expression levels found in cells that were cultured in either the progression of CMRL to F:12-DME medium described in this example or cells cultured in the media of this invention with the addition of 15 mM glucose.

Panel B shows the results of vimentin mRNA analysis on the primary cultures as described above. Vimentin is a fibroblast marker that is commonly used in the art, (see, e.g., Franke et al., Differentiation, 23(1):43-49 (1982), and Kahn et al., Cancer 51(4):645-53 (Feb. 15, 1983)). Consistent with the data above, cells cultured in the media of this invention expressed approximately half as much vimentin mRNA as compared to either cells cultured in CMRL and then F:12-DME medium as described in this example, or cells cultured in the media of this invention with the addition of 15 mM glucose.

Panel C shows the results of insulin mRNA analysis on the primary cultures as described above. Since these cells are primary pancreatic ductal cells, their insulin production capability should be preserved in culture. The primary culture cells in all three media conditions showed over 25,000 fold more insulin mRNA when compared to commercially purchased adult pancreatic cDNA. Although the insulin mRNA levels in the I3F cultured cells was the lowest, the mRNA level is still roughly within one standard deviation of the other two media conditions.

Additionally, the growth rate of the primary cultures as listed above was measured over the course of 8 days in culture, using an enzymatic assay that is correlative to cell number. Although in the earlier part of the culture the growth rate of the cells that were cultured in the media of this invention was slower, by the end of 8 days in culture, the cell number was substantially identical to the other two media conditions. Additionally, the cells cultured in the media of this invention appeared to be in log phase growth while the growth rate of cells in the other two conditions appeared to be leveling off, suggesting that these cells are entering into a quiescent phase.

I claim:

1. A composition of serum-free cell culture medium having the following components present at the indicated final concentrations: calcium chloride at 180 mg/L, potassium chloride at 298 mg/L, potassium nitrate at 0.0126 mg/L, magnesium sulfate at 68 mg/L, magnesium chloride at 37 mg/L, sodium chloride at 6200 mg/L, sodium bicarbonate at 1200 mg/L, sodium phosphate at 43 mg/L, sodium phosphate (dibasic) at 88 mg/L, sodium selenite at 0.0126 mg/L, ammonium metavanadate $3.51\times10^{-4}$ mg/L, molybdic acid at $3.72\times10^{-3}$ mg/L, cupric sulfate at $7.5\times10^{4}$ mg/L, ferrous sulfate at 0.25 mg/L, manganese sulfate at $4.53\times10^{-5}$ mg/L, zinc sulfate at 0.259 mg/L, fructose at 2000 mg/L, HEPES at 15 mM, putrescine at 0.048 mg/L, thioctic acid at 0.0618 mg/L, sodium pyruvate at 110.03 mg/L, linoleic acid at 0.025 mg/L, 1-alanine at 20.173 mg/L, 1-asparagine (freebase) at 17.5 mg/L, 1-asparagine at 122.01 mg/L, 1-aspartic acid at 24.99 mg/L, 1-cystine at 63.98 mg/L, 1-cysteine at 5.268 mg/L, glutamic acid at 56.9 mg/L, 1-glutamine at 600 mg/L, glycine at 23.25 mg/L, 1-histidine at 35.69 mg/L, 1-isoleucine at 74.68 mg/L, leucine at 77.43 mg/L, 1-lysine at 113.16 mg/L, 1-methionine at 22.34 mg/L, 1-phenylalanine at 47.69 mg/L, 1-proline at 38.36 mg/L, 1-seine at 32.55 mg/L, 1-threonine at 70.07 mg/L, 1-tryptophan at 11.81 mg/L, 1-tyrosine at 75.17 mg/L, 1-valine at 69.31 mg/L, biotin at $1.13\times10^{2}$ mg/L, D-Ca-pantothenate at 2.87 mg/L, choline chloride at 6.99 mg/L, folic acid at 3.2 mg/L, 1-inositol at 10.45 mg/L, niacinamide at 2.81 mg/L, pyriodxal at 2.8 mg/L, pyridoxine at $1.85\times10^{-2}$ mg/L, riboflavin at 0.291 mg/L, thiamine at 2.9 mg/L, vitamin $B_{12}$ at $4.99\times10^{-2}$ mg/L.

* * * * *

UNITED STATES PATENT AND TRADEMARK OFFICE
CERTIFICATE OF CORRECTION

PATENT NO. : 7,462,487 B2
APPLICATION NO. : 10/944083
DATED : December 9, 2008
INVENTOR(S) : Mary C. Tsao It is certified that error appears in the above-identified patent and that said Letters Patent is hereby corrected as shown below:

At column 20, line 13, the phrase "cupric sulfate at $7.5 \times 10^{4}$" should read as:

-- cupric sulfate at $7.5 \times 10^{-4}$ --.

At column 20, line 27, the phrase "biotin at $1.13 \times 102$" should read as:

-- biotin at $1.13 \times 10^{-2}$ --.

At column 20, line 30, the word "pyriodxal" should read as: -- pyridoxal --.

Signed and Sealed this

Fourth Day of May, 2010

David J. Kappos
*Director of the United States Patent and Trademark Office*